US011160577B2

United States Patent
Abbasi (10) Patent No.: US 11,160,577 B2
(45) Date of Patent: Nov. 2, 2021

(54) LATERAL DISC CUTTER

(71) Applicant: Advance Research System, LLC, Edina, MN (US)

(72) Inventor: Hamid R. Abbasi, Edina, MN (US)

(73) Assignee: Advance Research System, LLC, Edina, MN (US)

(*) Notice: Subject to any disclaimer, the term of this patent is extended or adjusted under 35 U.S.C. 154(b) by 436 days.

(21) Appl. No.: 16/052,535

(22) Filed: Aug. 1, 2018

(65) Prior Publication Data
US 2019/0038304 A1 Feb. 7, 2019

Related U.S. Application Data

(60) Provisional application No. 62/539,797, filed on Aug. 1, 2017.

(51) Int. Cl.
| A61B 17/32 | (2006.01) |
| A61B 17/16 | (2006.01) |
| A61B 17/3207 | (2006.01) |
| A61F 2/44 | (2006.01) |
| A61B 17/00 | (2006.01) |

(Continued)

(52) U.S. Cl.
CPC .... *A61B 17/32002* (2013.01); *A61B 17/1617* (2013.01); *A61B 17/1659* (2013.01); *A61B 17/1671* (2013.01); *A61B 17/320725* (2013.01); *A61B 2017/00261* (2013.01); *A61B 2017/320024* (2013.01); *A61B 2017/320028* (2013.01); *A61B 2017/320775* (2013.01); *A61F 2/4455* (2013.01); *A61F 2/46* (2013.01); *B23B 51/101* (2013.01); *Y10T 82/12* (2015.01); *Y10T 408/8588* (2015.01)

(58) Field of Classification Search
CPC ....... A61B 2017/320024; A61B 2017/320775; A61B 2017/00261; A61B 17/1671; A61B 17/1659; A61B 17/1617; A61B 17/00234; A61B 17/1615; A61B 17/32002; A61B 17/320725; A61B 2017/320028; A61F 2/4455; A61F 2/46; Y10T 408/8588; Y10T 408/858; Y10T 82/12; B23B 2250/04; B23B 51/101; B23D 77/044; B23C 2260/04; B23C 3/12; B23C 5/00
USPC .......... 606/79–85, 86 R, 167, 170, 171, 174; 408/152, 158, 181, 182, 183
See application file for complete search history.

(56) References Cited

U.S. PATENT DOCUMENTS

6,224,604 B1 * 5/2001 Suddaby ............ A61B 17/1615
 408/158
6,726,690 B2 4/2004 Eckman
(Continued)

*Primary Examiner* — Marcela I. Shirsat
(74) *Attorney, Agent, or Firm* — Christensen, Fonder, Dardi & Herbert PLLC (57) ABSTRACT

A lateral disc cutter for morcellating and decorticating tissue of an intervertebral disc from between adjacent vertebrae. The device can be arranged in a retracted configuration for insertion via an access tube, and in an extended configuration for cutting of tissue in the target region. The blades may be extended to contact the concave endplate in an orientation that is substantially parallel to a mid-plane of the intervertebral disc. Blades of the device may be configured with a convex profile that substantially conforms to the concave shape of the endplate for enhanced contact length between the blade and the endplate.

14 Claims, 7 Drawing Sheets

(51) Int. Cl.
*A61F 2/46* (2006.01)
*B23B 51/10* (2006.01)

(56) References Cited

U.S. PATENT DOCUMENTS

| | | | |
|---|---|---|---|
| 6,840,944 B2 * | 1/2005 | Suddaby | A61B 17/1671 |
| | | | 606/105 |
| 6,902,568 B2 * | 6/2005 | Serhan | A61B 17/1617 |
| | | | 606/79 |
| 7,329,267 B2 | 2/2008 | Weber | |
| 8,034,088 B2 | 10/2011 | Pagano | |
| 8,480,675 B2 | 7/2013 | Betts | |
| 8,551,097 B2 | 10/2013 | Schmitz et al. | |
| 8,568,416 B2 | 10/2013 | Schmitz et al. | |
| 8,579,902 B2 | 11/2013 | Bleich et al. | |
| 8,585,704 B2 | 11/2013 | Schmitz et al. | |
| 8,652,138 B2 | 2/2014 | Bleich et al. | |
| 8,663,228 B2 | 3/2014 | Schmitz et al. | |
| 8,845,639 B2 | 9/2014 | Wallace et al. | |
| 8,894,652 B2 | 11/2014 | Seifert et al. | |
| 9,247,952 B2 | 2/2016 | Bleich et al. | |
| 9,314,253 B2 | 4/2016 | Mimran et al. | |
| 9,320,618 B2 | 4/2016 | Schmitz et al. | |
| 9,326,777 B2 | 5/2016 | Tally | |
| 9,345,491 B2 | 5/2016 | Bleich et al. | |
| 9,351,741 B2 | 5/2016 | Schmitz et al. | |
| 9,456,829 B2 | 10/2016 | Saadat et al. | |
| 9,463,029 B2 | 10/2016 | Schmitz et al. | |
| 9,463,041 B2 | 10/2016 | Bleich et al. | |
| 2003/0135218 A1 * | 7/2003 | Eckman | A61B 17/1671 |
| | | | 606/79 |
| 2003/0220650 A1 | 11/2003 | Major et al. | |
| 2004/0122457 A1 | 6/2004 | Weber | |
| 2006/0116690 A1 | 6/2006 | Pagano | |
| 2008/0249552 A1 | 10/2008 | Eliachar et al. | |
| 2011/0015635 A1 * | 1/2011 | Aryan | A61B 17/1671 |
| | | | 606/84 |
| 2015/0173917 A1 | 6/2015 | Radcliffe et al. | |
| 2015/0306348 A1 | 10/2015 | Wallace et al. | |
| 2016/0030060 A1 | 2/2016 | Tally et al. | |
| 2017/0014142 A1 | 1/2017 | Schmitz et al. | |

* cited by examiner

LATERAL DISC CUTTER

RELATED APPLICATIONS

This application claims the benefit of U.S. Provisional Application No. 62/539,797, filed Aug. 1, 2017, the disclosure of which is hereby incorporated by referenced in its entirety.

FIELD OF THE DISCLOSURE

The disclosure relates generally to surgical instruments and techniques for treatment of the spine, and more specifically to tools and techniques for morcellation and decortication of disc tissue.

BACKGROUND

Techniques for the fusion of adjacent spinal vertebrae often involve promoting the growth of bony tissue between the endplates of the adjacent vertebrae. Growth of bony tissue is best facilitated by removing the tissue of the intervertebral disc that is in contact with the end plates, so that a clear path between adjacent endplates, and filling the resulting space with bone growth promoters, such as bone graft material (in addition to other spinal fusion appurtenances, such as fusion cages). The bone growth promoter typically extends between and contacts the endplates. The greater the exposed surface area of the vertebral endplates prior to implanting the bone growth promoter, the better.

Removing bone tissue from and between the endplates for satisfactory exposure of the endplate bone can be a time consuming process. As with all surgical procedures, reducing the time required to perform a surgical step is at a premium. An apparatus and technique that reduces the decortication and morcellation of intervertebral discs in spinal fusion procedures would be welcomed.

SUMMARY

Various embodiments of the disclosure provide a mechanism that orient one or more morcellating blades to remain substantially parallel to a mid-plane of the intervertebral disc as the mechanism extends the blade(s) in the superior/inferior direction and into contact with a vertebral endplate. Accordingly, the blades are oriented for enhanced contact relative to morcellating blades of the prior art. In some embodiments, the blades of the device are configured with a convex profile that substantially conforms to the concave shape of the endplate for enhanced contact between the blade and the endplate during decortication of the intervertebral disc.

Conventional disc cutters for morcellating intervertebral discs tend to fan radially outward from a pivot point close to a central axis of the access tube. Such conventional disc cutters provide a cutting edge that contacts the vertebral endpoints along an inherently limited span. Accordingly, conventional disc cutters require several passes of the blade to sufficiently prepare the intervertebral space for spinal fusion procedures. The lateral disc cutter of the present disclosure increases the line of contact between the blade and the vertebral endplate, thus requiring fewer scraping passes to properly prepare the vertebral endplate.

DETAILED DESCRIPTION OF THE FIGURES

Figures 1, 1A:
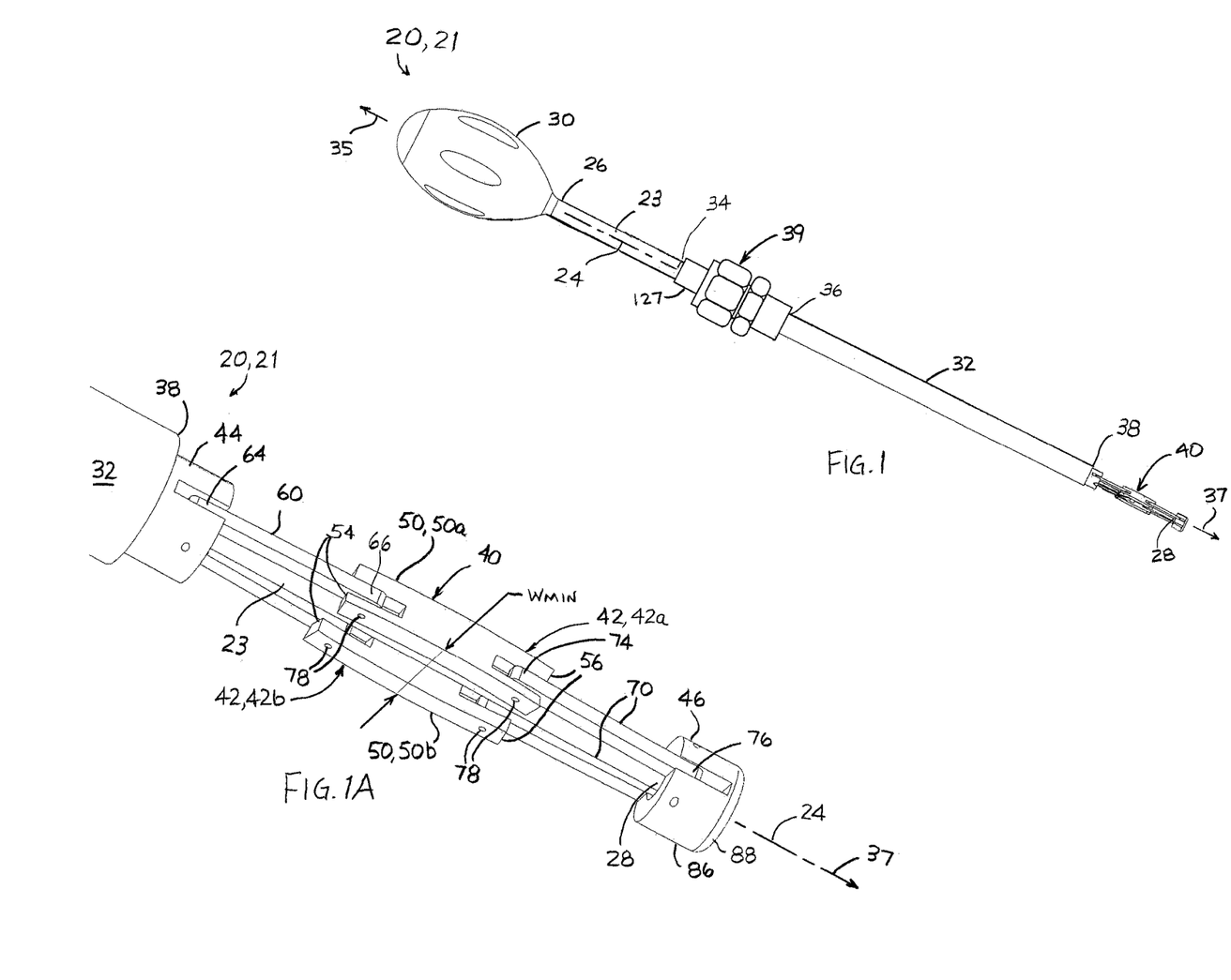
FIG. 1 is a perspective view of a lateral disc cutter in a retracted configuration according to an embodiment of the disclosure.
FIG. 1A is an enlarged view of cutter assemblies at a distal end of the lateral disc cutter in the retracted configuration of FIG. 1.
Figures 2, 2A:
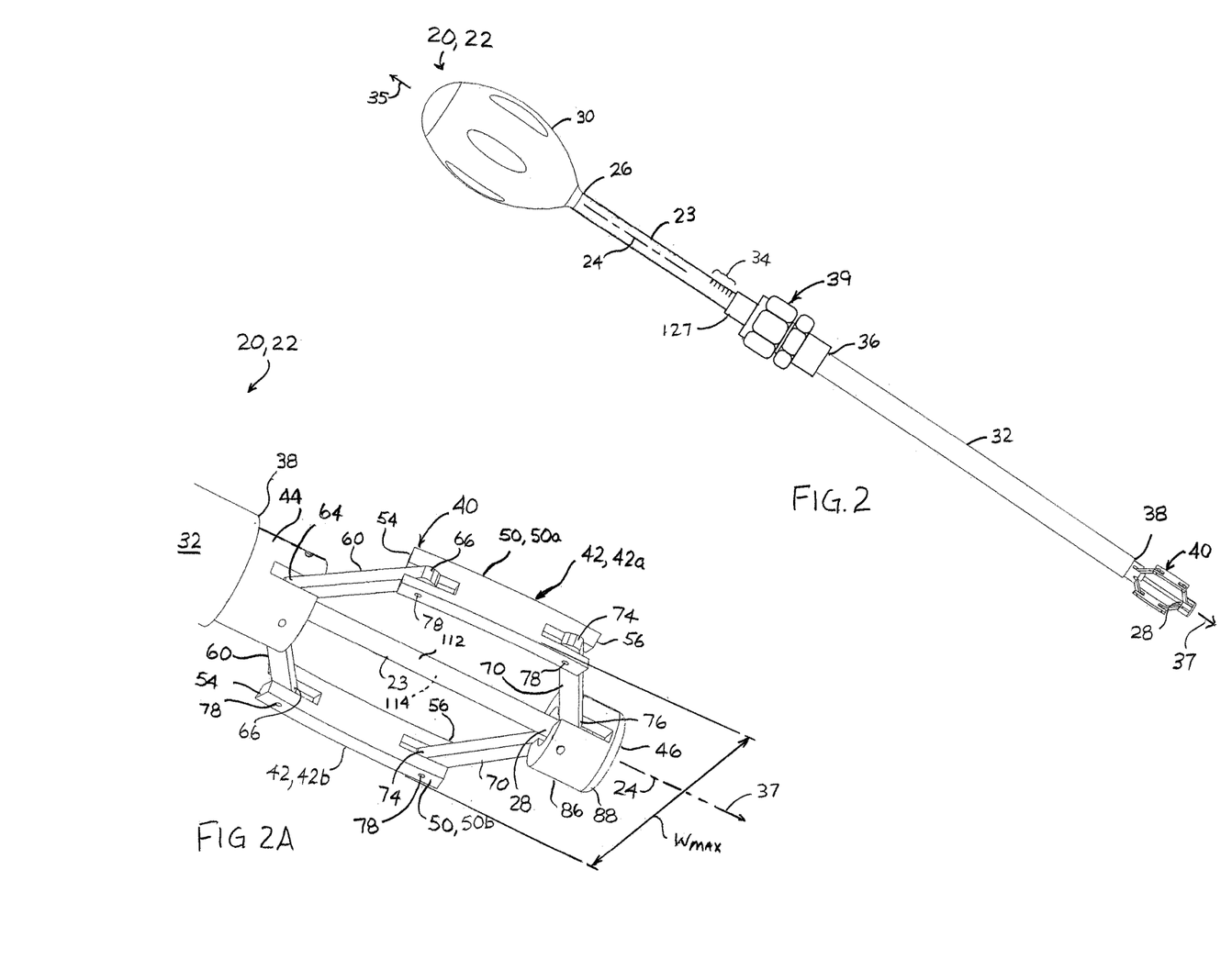
FIG. 2 is a perspective view of the lateral disc cutter of FIG. 1 in a fully extended configuration according to an embodiment of the disclosure.
FIG. 2A is an enlarged view of cutter assemblies at a distal end of the lateral disc cutter in the fully extended configuration of FIG. 2.

Referring to FIGS. 1 and 2, a lateral disc cutter 20 for removing tissue between adjacent vertebrae of a spine is depicted in a fully retracted configuration 21 and a fully extended configuration 22, respectively, according to embodiments of the disclosure. The lateral disc cutter 20 includes a stem 23 that defines an actuation axis 24 and includes a proximal end 26 and a distal end 28. The proximal end 26 may be fitted with a knob or handle 30. The distal end 28 extends through a sleeve 32, the stem 23 being translatable within the sleeve 32 in a proximal direction 35 and a distal direction 37. In some embodiments, the stem 23 is also rotatable within the sleeve 32. The sleeve 32 includes a proximal end 36 and a distal end 38, and may include a stem lock assembly 39 affixed to the proximal end 36. In some embodiments, the stem 23 includes graduation lines 34 formed on a portion of the stem 23 that translates into and out of the a sight tube 127 of the stem lock assembly 39 (or, when no stem lock assembly 39 is utilized, the proximal end 36 of the sleeve 32). A morcellator assembly 40 is affixed to the distal end 38 of the sleeve 32 and is coupled to the stem 23.

Referring to FIGS. 1A and 2A, the morcellator assembly 40 is depicted in greater detail. The morcellator assembly 40 includes at least one cutter assembly 42 pivotally mounted to a proximal collar or hub 44 and to a distal collar or hub 46. Each cutter assembly 42 includes a cutter or blade 50 having a proximal end 54 and a distal end 56, a proximal linkage 60 having a proximal end 64 and a distal end 66, and a distal linkage 70 having a proximal end 74 and a distal end 76. The proximal end 64 of the proximal linkage 60 is pivotally connected to the proximal hub 44. The distal end 66 of the proximal linkage 60 is pivotally connected the proximal end 54 of the blade 50. The distal end 76 of the distal linkage 70 is pivotally connected to the distal hub 46, and the proximal end 74 of the distal linkage 70 is pivotally connected to the distal end 56 of the blade 50. The pivotal connections may be accomplished, for example, by using hinge pins 78 that are affixed to the hubs 44, 46 and blade 50, and about which the linkages 60 and 70 freely rotate.

Figure 10:
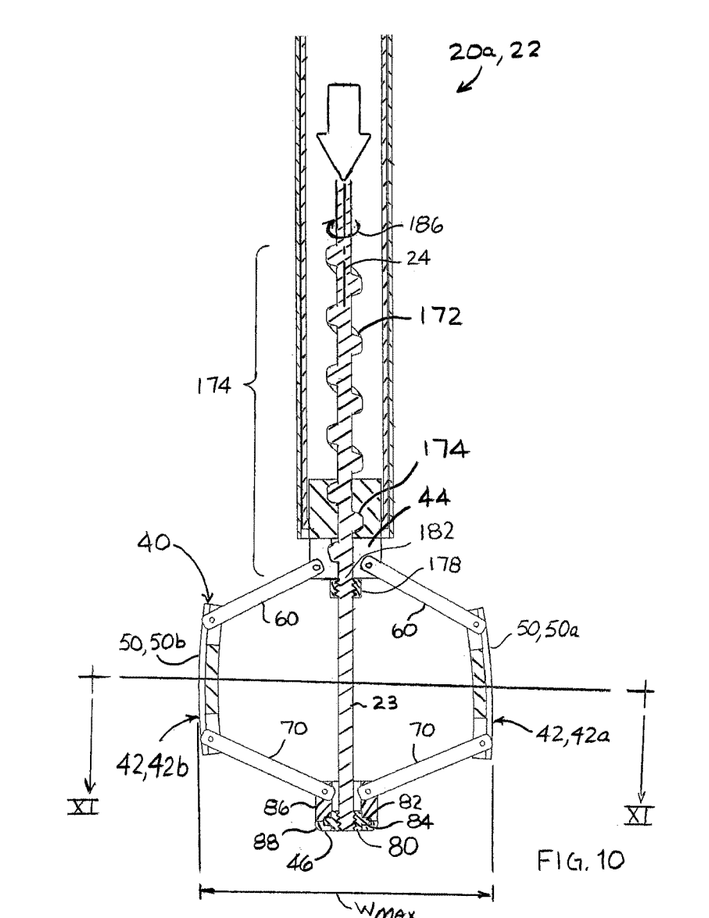
FIG. 10 is a sectional view of the screw driven lateral disc cutter of FIG. 9 in an extended configuration according to an embodiment of the disclosure.

The stem 23 and the proximal hub 44 are configured to enable translation of the stem 23 through the proximal hub 44. In some embodiments, the stem is also rotatable within proximal hub 44. The distal end 28 of the stem 23 is captured within the distal hub 46, and may also be rotatable within the distal hub 46. In some embodiments, the distal end of the stem 23 includes or is fitted with a head portion 80 (FIG. 10). The head portion 80 may be oversized (depicted), undersized, or the same diameter as the stem 23, and may include a retention feature 82 (e.g., a flange) that is captured within a race 84 defined by the distal hub 46. The distal hub 46 may include a body portion 86 and an end cap 88 that cooperate to capture the head portion 80 within the distal hub 46.

The lateral disc cutter 20 is configured in the fully retracted configuration 21 (FIG. 1) by translating the stem 23 in the distal direction 37, until the cutter assembly 42 is pulled taut in the distal direction 37. The translation of the stem 23 also translates the distal hub 46 away from the proximal hub 44, thereby elongating the cutter assembly or assemblies 42 and drawing the blade 50 radially inward, toward the actuation axis 24. The lateral disc cutter 20 is configured in the fully extended configuration 22 (FIG. 2) by translating the stem in the proximal direction 35 until the blades 50 reach a maximum lateral displacement away from the actuation axis 24.

The translation of the stem 23 causes the graduation lines 34 to slide through a sight tube 127 of the stem lock assembly 39 (or alternatively, proximal end 36 of the sleeve 32) in succession. In some embodiments, each graduation line 34 includes a numerical label that corresponds to a displacement width W (e.g., in millimeters) of the morcellator assembly 40 when the respective graduation line 34 is aligned with the proximal end 36 of the sleeve 32. This tells the operator what the cutting span of the morcellator assembly 40 is at a given axial displacement of the stem 23 within the sleeve 32. Alternatively, the graduation lines 34 may include numerical labels that correspond to a length scale (e.g., millimeters), indicating the displacement of the stem 23 within the sleeve 32.

In some embodiments, when in the fully retracted configuration, the minimum displacement width WMIN of the morcellator assembly 40 is in a range of 6 millimeters (mm) to 8 mm inclusive. In some embodiments, when in the fully extended configuration, the maximum displacement width WMAX of the morcellator assembly 40 is in a range of 6 millimeters (mm) to 8 mm inclusive. Herein, a range that is said to be "inclusive" includes the stated endpoints of the range, as well as a values between the endpoints. Also herein, the displacement width "W" refers generically to any displacement width from WMIN to WMAX inclusive.

Figure 3:
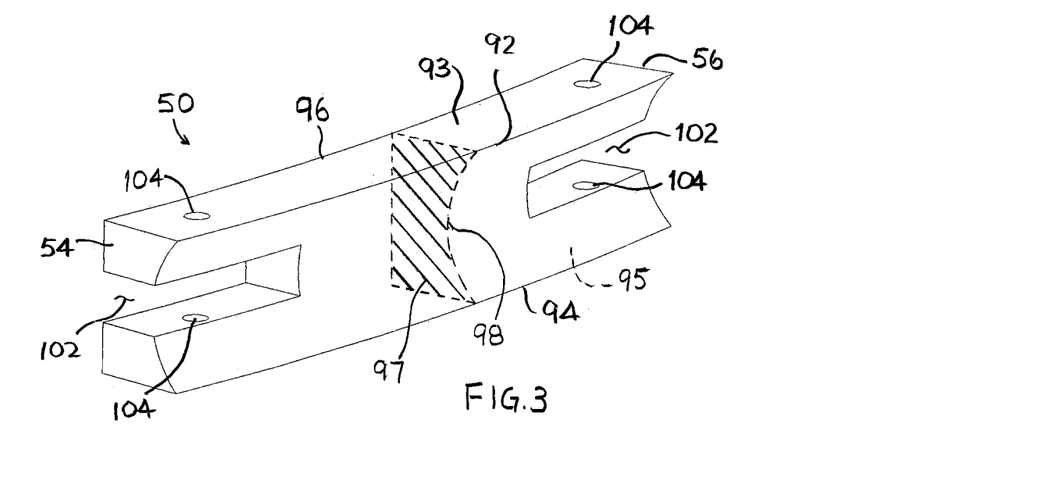
FIG. 3 is a perspective view of an arcuate cutting blade in isolation according to an embodiment of the disclosure.
Figure 4:
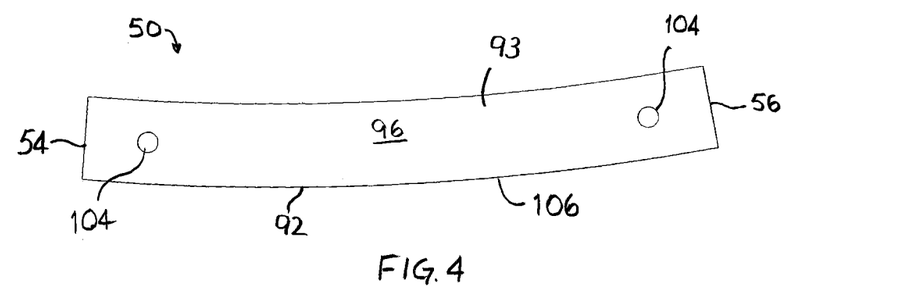
FIG. 4 is a plan view of the arcuate cutting blade of FIG. 3 according to an embodiment of the disclosure.

Referring to FIGS. 3 and 4, the blade 50 is depicted and described in more detail according to an embodiment of the disclosure. In the depicted embodiment, each blade 50 defines a first cutting edge 92 that borders a first surface 93 and extends from the proximal end 54 to the distal end 56 of the blade 50, and a second cutting edge 94 that borders a second surface 95 that also extends from the proximal end 54 to the distal end 56 of the blade 50, such that the first cutting edge 92 and the second cutting edge 94 extend in a direction that is substantially parallel to the actuation axis 24. In some embodiments, each of the blades 50 is an elongate, rigid block 96 having a cross-section 97 that defines a concave surface 98 between the first cutting edge 92 and the second cutting edge 94. The concave surface 98 may be arcuate, as depicted in FIG. 3. The concave surface 98 faces away from the actuation axis 24. The proximal and distal ends 54 and 56 of the blade 50 may each define a slot 102 that extends axially into the block 96 parallel to the first and second surfaces 93 and 95, and a mounting hole 104 that extends through the slot 102 and through the first and second surfaces 93 and 95. In some embodiments, the cutting edges 92 and 94 each define a convex profile 106 that bows laterally outward, away from the actuation axis 24. Alternatively, the profile of the cutting edges 92, 94 may be linear.

The morcellator assembly 40 may have a single blade 50 or a plurality of blades 50 and cutter assemblies 42, such as a pair of blades 50a, 50b and cutter assemblies 42a, 42b depicted in the figures. In some embodiments, a first blade 50a of the pair of blades 50a, 50b is disposed adjacent a first side 112 of the stem 23 and a second blade 50b of the pair of blades 50a, 50b is disposed adjacent a second side 114 of the stem 23 (FIG. 2A). In some embodiments, the first side 112 and the second side 114 of the stem 23 are diametrically opposed. Other arrangements for a plurality of blades 50 are also contemplated, for example a three- or four-blade arrangement with the blades 50 distributed tangentially about the stem 23.

In assembly, the proximal hub 44 is affixed to the distal end 38 of the sleeve 32, for example by welding, crimping, pins, set screw, or threaded engagement. The proximal linkages 60 are pivotally coupled to the proximal hub 44 and the blades 50, and the distal linkages 70 pivotally coupled to the distal hub 46. With the end cap 88 removed, the distal end 28 of the stem 23 may be inserted into the proximal end 36 of the sleeve 32, through the distal end 38 of the sleeve 32, and through the hubs 44 and 46. For oversized head portions 80 (depicted), the head portion 80 can be removed during the insertion. With the distal end 28 of the stem 23 extending through the distal hub 46, the head portion 80 may be affixed to the distal end 28, the head portion 80 seated in the body portion 86 of the distal hub 46, and the end cap 88 secured to the body portion 86 to capture the head portion 80 and retention feature 82 within the distal hub 46. The handle 30 is affixed to the proximal end 26 of the stem 23.

Figure 5:
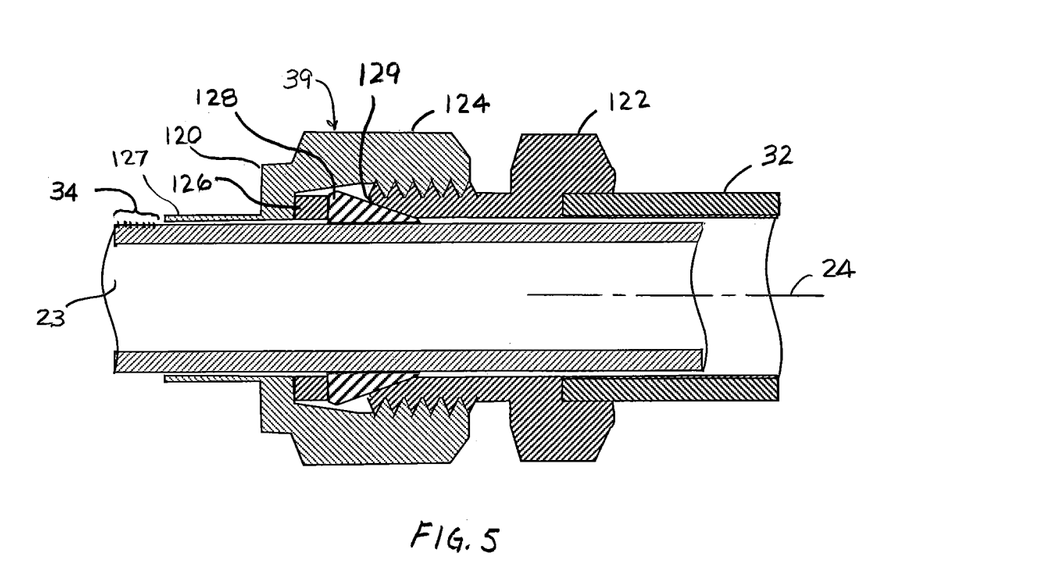
FIG. 5 is a sectional view a stem lock assembly of the lateral disc cutter of FIG. 1 according to an embodiment of the disclosure.

Referring to FIG. 5, the stem lock assembly 39 is depicted in greater detail according to an embodiment of the disclosure. In some embodiments, the stem lock assembly 39 includes a compression fitting 120 having a male threaded fitting 122, a cap nut 124, a slip ring 126, and a ferrule 128. The male threaded fitting 122 is affixed to the proximal end 36 of the sleeve 32, for example by welding, gluing, or a threaded coupling. The cap nut 124 threadably engages the male threaded fitting 122 and, when rotated, may slide over the slip ring 126. Tightening the cap nut 124 to the male threaded fitting 122 forces the ferrule 128 into a flared end 129 of the male threaded fitting 122, causing it to compress radially inward against the stem 23, thereby locking the stem 23 at an axial location within and relative to the sleeve 32. In some embodiments, the ferrule 128 is of a polymer material (e.g., NYLON), which yields under compression instead of dimpling of the stem 32. The stem lock assembly 39 may also include a sight tube 127 that protrudes proximally and aligns with the graduation lines 34 for easy reading of the displacement of the stem 23 relative to the sleeve 32 in operation. The depiction of FIG. 5 presents the male threaded fitting 122 and the cap nut 124 as having flats. It is understood that other external forms may be implemented for the male threaded fitting 122 and the cap nut, for example, a knurled cylinder.

Figure 6:
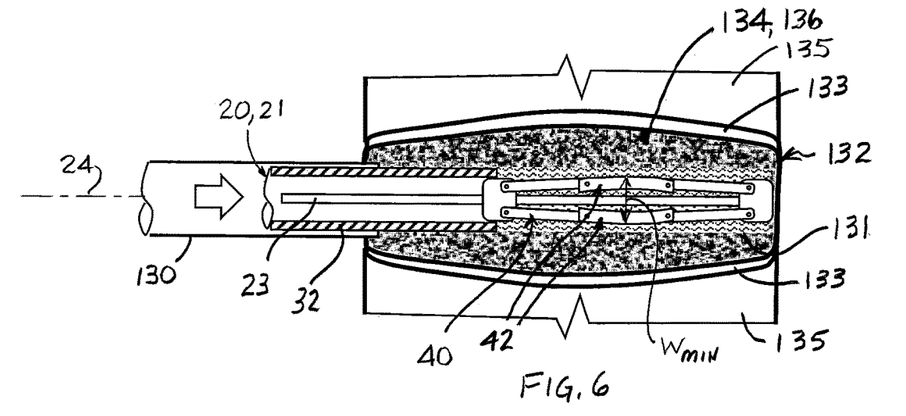
FIGS. 6 through 8 are lateral view schematics of a procedure for morcellating tissue in a disc nucleus with a lateral disc cutter of the present disclosure according to an embodiment of the disclosure.
Figure 7:
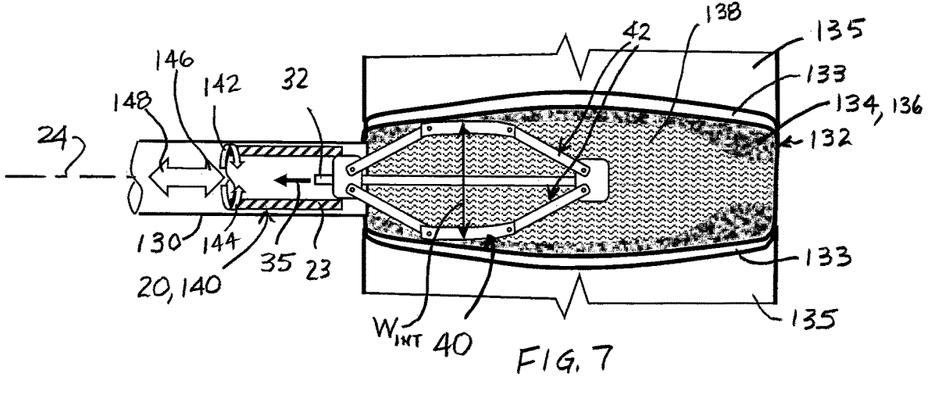
Figure 8:
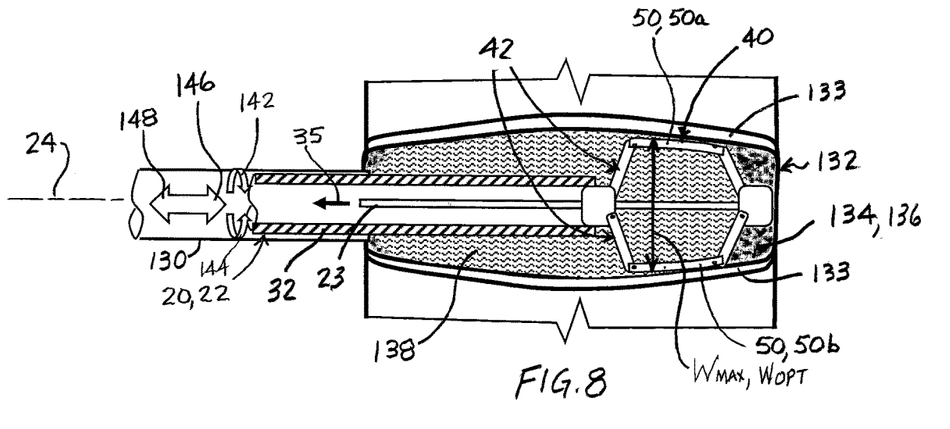

Referring to FIGS. 6 through 8, operation of the lateral disc cutter 20 is depicted according to an embodiment of the disclosure. An access tube 130 is surgically inserted into an intervertebral disc 132 that is disposed between the endplates 133 of adjacent vertebrae 135, providing access to a nucleus 134 of the intervertebral disc 132. A core passage 131 is cut through the intervertebral disc 132 using standard tools and techniques available to the artisan, the core passage 131 having a diameter that approximates the inner diameter of the access tube 130. With the lateral disc cutter 20 in the fully retracted configuration 21, the lateral disc cutter 20 is inserted through the access tube 130 so that the morcellator assembly 40 extends into the core passage 131 (FIG. 6).

The morcellator assembly 40 may be configured in a partially extended configuration 140 (FIG. 7) by translating the stem 23 in the proximal direction 35, causing the cutter assembly 42 to flex outward and increase the displacement width W of the morcellator assembly 40. In the partially extended configuration 140, an intermediate displacement width WINT is attained that is between the values of WMIN in the fully retracted configuration 21 and WMAX in the fully extended configuration 22. For embodiments including the stem lock assembly 39, the stem lock assembly 39 may be set, which releasably fixes the stem 23 relative to the sleeve 32 and enables the lateral disc cutter 20 to be rotated as a unit by the handle 30 without altering or disturbing the displacement width W of the morcellator assembly 40. Securing the stem 23 relative to the sleeve 32 enables the lateral disc cutter 20 to be rotated about the actuation axis 24. Rotation of the lateral disc cutter 20 may be back and forth (i.e., alternating between clockwise and counterclockwise motion about the actuation axis 24) as represented by arrows 142 and 144.

In the partially extended configuration 140, the morcellator assembly 40 cuts into the core tissue 136 adjacent the core passage 131 to increase the region of morcellated tissue 138. The lateral disc cutter 20 may also be reciprocated fore and aft (i.e., in the generally posterior and anterior directions 146 and 148) within the disc nucleus 134 to further expand the region of morcellated tissue 138.

To increase the reach of the morcellator assembly 40 in the superior and inferior directions, the displacement width W of the morcellator assembly 40 is increased. The stem lock assembly 39 (when utilized) is released and the stem 32 translated in the proximal direction 35 until the desired displacement width W is attained. During this step, the graduation lines 134 may be used in conjunction with the sight tube 127 to inform the user of the displacement width W (e.g., FIG. 1). Upon reaching the desired displacement width W, the stem lock assembly 39 (when utilized) is reset and the process of rotating the lateral disc cutter 20 about the actuation axis 24 and, optionally, reciprocating the lateral disc cutter 20 in the posterior and anterior directions 146 and 148 is repeated, thereby increasing the region of morcellated tissue 138.

The process of releasing the stem lock assembly 39, expanding the morcellator assembly 40, and resetting the stem lock assembly 39, followed by rotation and reciprocation of the morcellator assembly 40 within the disc nucleus 134 is repeated until the morcellator assembly 40 reaches the fully extended configuration 22 (FIG. 8), or an optimum displacement width WOPT limited by the dimension between the adjacent vertebrae 135. When the displacement width WMAX or WOPT is such that the blades 50a and 50b contact the respective endplates 133 of the adjacent vertebrae 135, the morcellator assembly 40 may be used to cut through the outer tissue of the intervertebral disc 132 to scrape the bone tissue of the endplates 133. The convex profiles 106 of the blades 50 approximate the concave face of the endplates 133. Also, the each cutter assembly 42 extends the respective blade 50 in an orientation that is generally parallel to a mid-plane of the intervertebral disc space, and providing contact with the respective endplate 133 that extends over a substantial portion of the blade 50. By this process, wide swaths of tissue at the boundary of the endplate 133 and the intervertebral disc 132 are decorticated from the intervertebral disc 132 and scraped off the endplates 133.

Once the morcellation and decortication is complete, the lateral disc cutter 20 is reconfigured in the fully retracted configuration 21 and withdrawn through the access tube 130. The morcellated tissue 138 may be withdrawn through the access tube 130, for example with a suction device.

Functionally, the fully retracted configuration 21 reduces the profile of the morcellator assembly to enable insertion through the access tube 130 in a minimally invasive surgical procedure. The tissue scraped from the endplates 133 may gather within the concavity provided by the concave surface during a scraping stroke. Also, the concave surface 98 of the blades 50 provide relief for the core tissue 136 as it is morcellated, preventing the cutting edges 92, 94 from fouling due to accumulation of compacted tissue. The relief provided by the concave surface 98 enables the tissue compressed by the rotational advancement of the surfaces 93 and 95 of the blades 50 during morcellation, to expand into the cavity defined by the concave surface 98 after being cut. This may inhibit fouling of the cutting edges 92, 94. The convex profiles 106 of the blades 50 may conform closely to the concave surfaces of the endplates 133 for morcellating tissue closer to the endplates 133. The convex profile 106 may also act as a lead-in that guides the morcellator assembly 40 back into the access tube 130 when withdrawing the lateral disc cutter 20.

Figure 9:
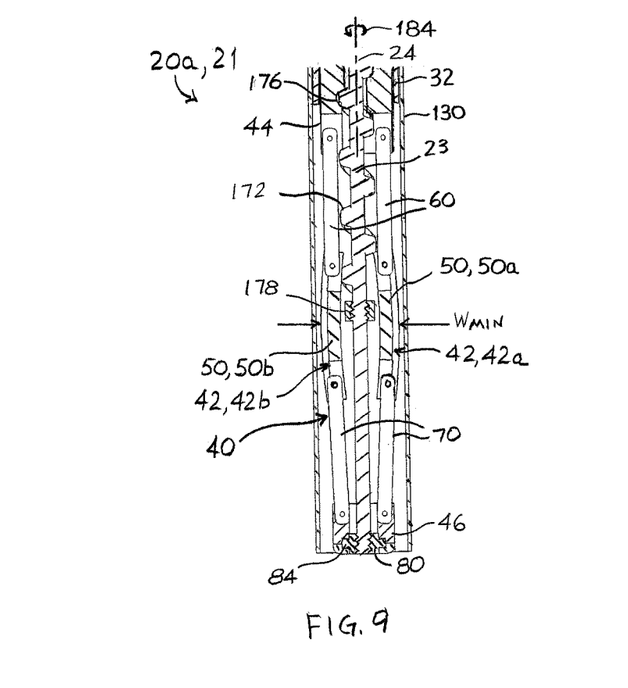
FIG. 9 is a partial sectional view of a screw driven lateral disc cutter in a retracted configuration according to an embodiment of the disclosure.

Referring to FIGS. 9 and 10, a partial view of a lateral disc cutter 20a is depicted in the fully retracted configuration 21 and the fully extended configuration 22, respectively, according to embodiments of the disclosure. The lateral disc cutter 20a includes many of the same components and attributes as the lateral disc cutter 20, which are indicated with same-numbered reference characters. Only the distal portion of the lateral disc cutter 20a is portrayed in FIGS. 9 and 10. The proximal portion (not depicted) of the lateral disc cutter 20a may be of the same construction as the lateral disc cutter 20. Also in FIGS. 9 and 10, operation of the disc cutter 20a relative to the access tube 130 is depicted.

For the lateral disc cutter 20a, the stem 23 includes external thread 172 that define a threaded region 174 of the stem 23. The proximal hub 44 may include an internal thread 176 that are threadably engaged with the external thread 172 of the stem 23. In some embodiments, the stem 23 includes or is fitted with a stop 178 at a distal end 182 of the threaded region 174, the stop 178 being distal to the proximal hub 44. The stop 178 may be affixed to the stem 23 in a variety of ways available to the artisan, including threaded engagement (depicted), press fitting over an enlarged diameter portion of the stem 23, welding, with pins, with a set screw, or by gluing.

In operation, the lateral disc cutter 20a is pushed through the access tube 130 so that the morcellator assembly 40 extends out of the distal end of the access tube 130. The external thread 172 of the stem 23 cooperates with the internal thread 176 of the proximal hub 44 for axially translating and positioning the stem 23 relative to the sleeve 32. For the lateral disc cutter 20a, the proximal hub 44, being affixed to the sleeve 32, remains stationary during rotation of the stem 23. During the rotation/translation of the stem 23, the head portion 80 and retention feature 82 are rotated within the distal hub 46 for the lateral disc cutter 20a.

Rotation of the stem 23 in a first rotational direction 184 causes the rotating stem 23 to translate in the proximal direction 35 which draws the distal hub 46 toward the proximal hub 44, thereby causing the proximal linkage 60 and the distal linkage 70 to pivot away from the stem 23 and translate the blade 50 away from the stem 23 and toward the fully extended configuration 22.

When rotating the stem 23 in the first rotational direction 184, proximal translation of the stem 23 reaches a limit when the stop 178 engages a distal face of the proximal hub 44. In such embodiments, engagement of the stop 178 with the proximal hub 44 establishes the fully extended configuration 22.

Rotation of the stem 23 in a second rotational direction 186 that is opposite the first rotational direction 184 translates the distal hub 46 away from the proximal hub 44, thereby causing the proximal linkage 60 and the distal linkage 70 to pivot toward the stem 23 and translate the blade 50 toward the stem 23 and toward the fully retracted configuration 21. When rotating the stem 23 in the second rotational direction 186, distal translation of the stem 23 reaches a limit when the cutter assemblies 42 are pulled taut between the proximal and distal hubs 44 and 46. For the lateral disc cutter 20a, the external thread 172 of the stem 23 extend through the proximal hub 44 when in the fully retracted configuration 21 and for all intermediate configurations between the fully retracted configuration 21 and the fully extended configuration 22.

Figure 11:
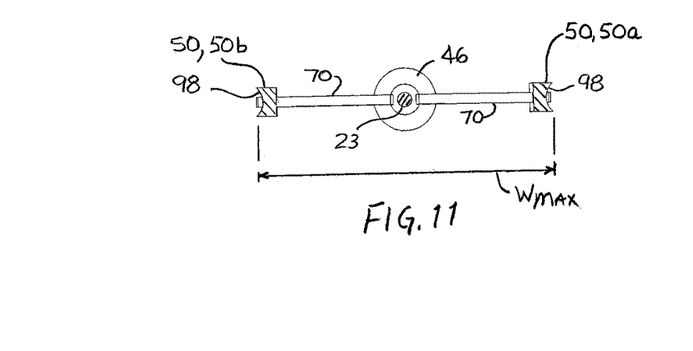
FIG. 11 is a sectional view of a morcellator assembly at plane XI-XI of FIG. 10 according to an embodiment of the disclosure.

Referring to FIG. 11, the stem 23 and blades 50 of the morcellator assembly 40 are depicted in cross-section according to an embodiment of the disclosure. The arrangement illustrates the concave surfaces 98 facing laterally away from the stem 23 and actuation axis 24.

Figure 12:
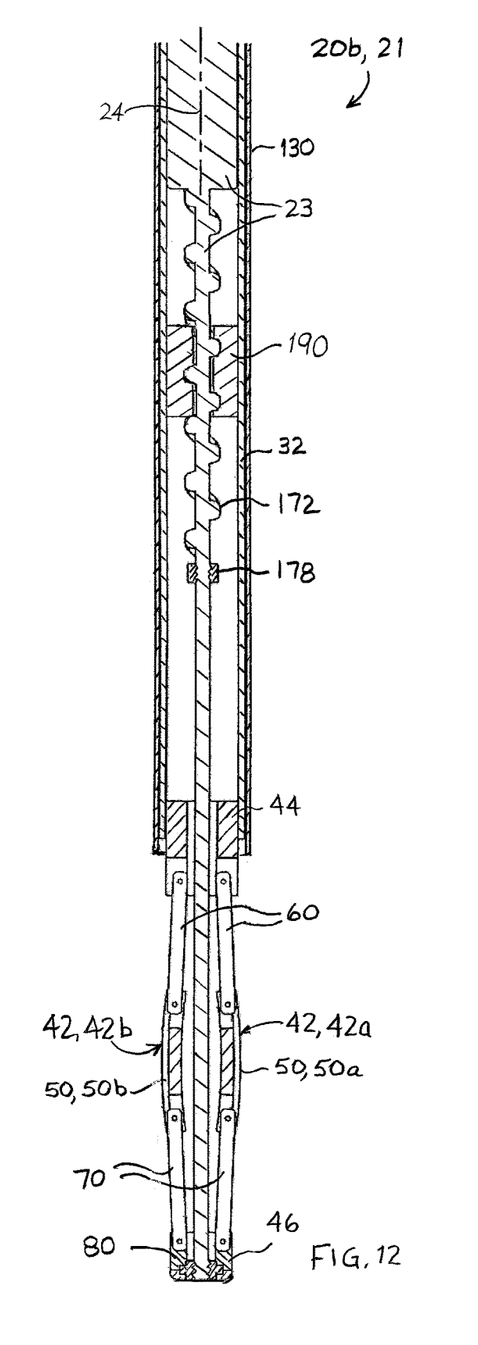
FIG. 12 is a sectional view of a screw driven lateral disc cutter with drive threads contained in a sleeve of the lateral disc cutter in a retracted configuration according to an embodiment of the disclosure.
Figure 13:
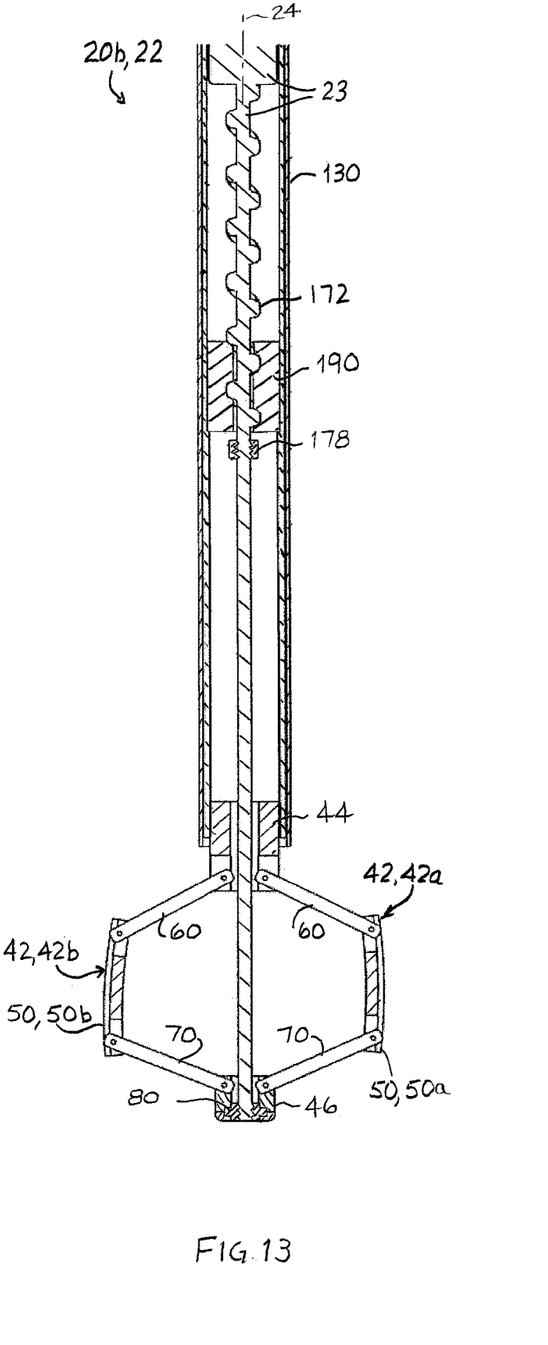
FIG. 13 is a sectional view of the screw driven lateral disc cutter of FIG. 12 in an extended configuration according to an embodiment of the disclosure.

Referring to FIGS. 12 and 13, a partial view of a lateral disc cutter 20b is depicted in the fully retracted configuration 21 and the fully extended configuration 22, respectively, according to embodiments of the disclosure. The lateral disc cutter 20b includes many of the same components and attributes as the lateral disc cutter 20a, which are indicated with same-numbered reference characters. Only the distal portion of the lateral disc cutter 20b is portrayed in FIGS. 12 and 13. The proximal portion of the lateral disc cutter 20b (not depicted) may be of the same construction as the lateral disc cutter 20. Also in FIGS. 12 and 13, the access tube 130 is depicted.

For the lateral disc cutter 20b, the external thread 172 of the stem 23 are disposed proximal to the proximal hub 44 and do not engage the proximal hub 44. Instead, a threaded insert 190 is disposed inside the sleeve 32 having internal threads 192 that engage the external thread 172. Also, the stop 178 may be disposed inside the sleeve 32 to engage the threaded insert 190 when the lateral disc cutter 20b is in the fully extended configuration 22. Accordingly, neither the external thread 172 nor the stop 178 extend outside the sleeve 32 during operation.

In assembly, the threaded insert 190 may be welded, glued, or crimped to the sleeve 32. Optionally, the threaded insert 190 may be manufactured as unitary with the sleeve 32. Optionally, the sleeve may be in multiple parts, with the threaded insert 190 including external threads to which the two parts are threadably engaged to form a joint at the threaded insert 190 (not depicted).

Figure 14:
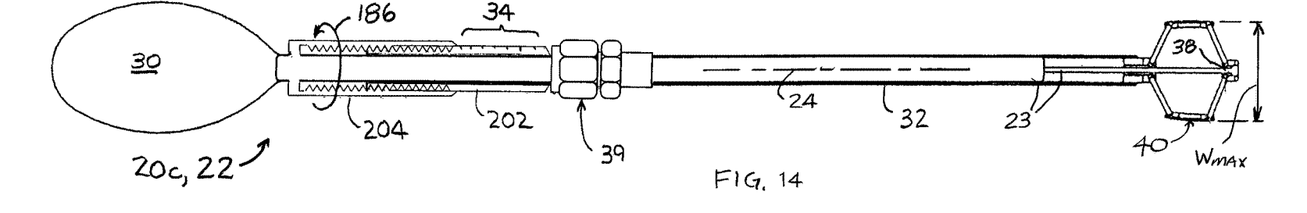
FIG. 14 is a sectional view of a screw driven lateral disc cutter with external drive threads at a proximal end and in an extended configuration according to an embodiment of the disclosure.
Figure 15:
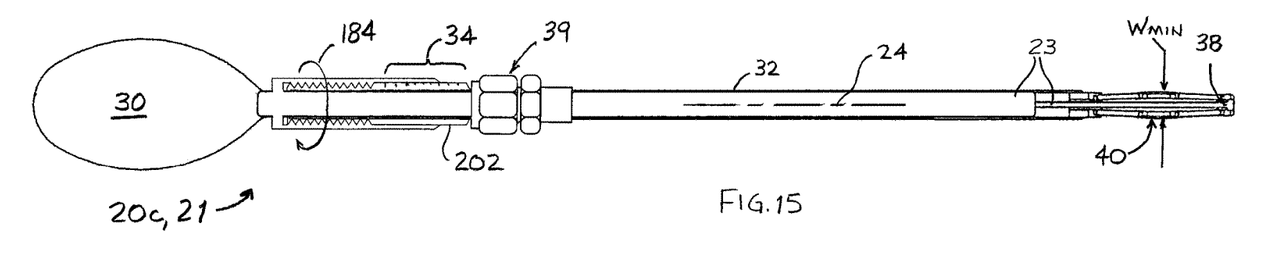
FIG. 15 is a sectional view of the screw driven lateral disc cutter of FIG. 14 in a retracted configuration according to an embodiment of the disclosure.
Figure 16:
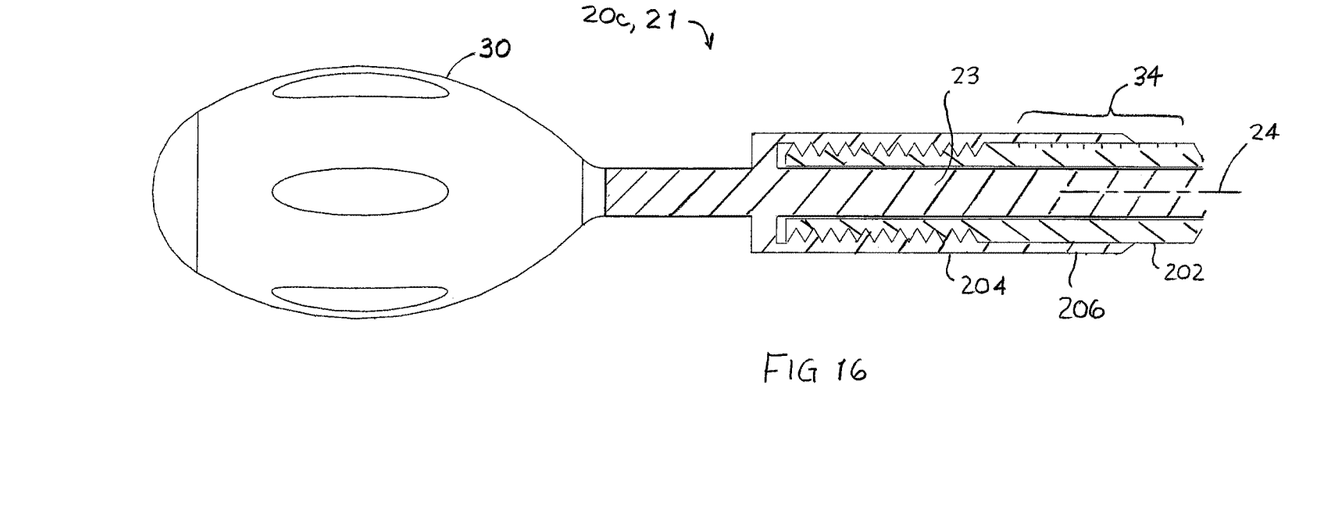
FIG. 16 is a partial sectional view of the proximal end of the lateral disc cutter of FIG. 15 in the fully extended configuration according to an embodiment of the disclosure.

Referring to FIGS. 14 through 16, a lateral disc cutter 20c is depicted in the fully extended configuration 22 and the fully retracted configuration 21, respectively, according to embodiments of the disclosure. The lateral disc cutter 20c includes many of the same components and attributes as the lateral disc cutter 20, which are indicated with same-numbered reference characters. The lateral disc cutter 20c includes a first threaded fitting 202 disposed at the proximal end of the stem lock assembly 39 that mates with a second threaded fitting 204 affixed to the stem 23 near the proximal end 26. Translation of the stem 23 relative to the sleeve 32 is accomplished by rotation of the stem 23 via handle 30, which adjusts and positions the second threaded fitting 204 axially along the first threaded fitting 202. The relative positioning of the threaded fittings 202, 204 positions the distal end 38 of the stem 23 for manipulating the morcellator assembly 40 and affecting a desired displacement width W. In some embodiments, the graduation lines 34 are disposed on the first threaded fitting 202, with the second threaded fitting 204 including a sight tube 206 that protrudes distally and aligns with the graduation lines 34 for easy reading of the displacement of the stem 23 relative to the sleeve 32 in operation.

In some embodiments, at least some of the operational steps of the lateral disc cutter 20 attendant to FIGS. 6 through 8 are provided as instructions that are provided along with any one of the lateral disc cutters 20, 20a, 20b, and 20c as a kit. Optionally, the access tube 130 may also be provided with the kit. Optionally, at least some of the operation of the screw driven lateral disc cutters 20a, 20b, and 20c may also be included with the instructions. The instructions are provided on a non-transitory medium, such as paper or a magnetic storage medium in computer readable format.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art. Herein, references to "proximal" and associated derivative terms refer to a direction or position that is toward the surgeon or operator. References to "distal" and associated derivative terms refer to a direction or position that is away from the surgeon or operator.

For purposes of interpreting the claims, it is expressly intended that the provisions of 35 U.S.C. 112(f) are not to be invoked unless the specific terms "means for" or "step for" are recited in the respective claim.

What is claimed is:

1. A surgical instrument for removing tissue between adjacent vertebrae of a spine, comprising:
    a stem that defines an actuation axis;
    a sleeve concentric about said actuation axis, said stem being translatable within said sleeve along said actuation axis;
    a proximal hub in fixed relation to a distal end of said sleeve, said stem extending through and being translatable in a proximal and a distal direction through said proximal hub;
    a distal hub coupled to a distal end of said stem; and
    at least one cutter assembly, each including:
        a blade having a proximal end and a distal end, said blade being parallel to said actuation axis of said stem;
        a proximal linkage pivotally connected to said proximal hub and pivotally connected to said proximal end of said blade; and
        a distal linkage pivotally connected to said distal hub and pivotally connected to said distal end of said blade,
    wherein said at least one cutter assembly is configured so that translation of said stem in said proximal direction causes said distal hub to translate toward said proximal hub and causes said proximal linkage and said distal linkage to pivot away from said stem for translation of said blade laterally away from said stem, said blade remaining parallel to said actuation axis of said stem during said translation of said blade laterally away from said stem, and
    wherein said at least one cutter assembly is configured so that translation of said stem in said distal direction causes said distal hub to translate away from said proximal hub and causes said proximal linkage and said distal linkage to pivot toward said stem for translation of said blade laterally toward said stem, said blade remaining substantially parallel to said actuation axis of said stem during said translation of said blade laterally toward said stem.

2. The surgical instrument of claim 1, wherein said blade defines a first cutting edge that extends from said first end to said second end and a second cutting edge that extends from said first end to said second end, said first cutting edge and said second cutting edge extending in a direction parallel to said actuation axis.

3. The surgical instrument of claim 2, wherein said first cutting edge and said second cutting edge defines a convex profile that is convex in a lateral direction that points away from said actuation axis.

4. The surgical instrument of claim 2, wherein said blade is an elongate, rigid block that defines a concave surface between said first cutting edge and said second cutting edge, said concave surface facing away from said actuation axis.

5. The surgical instrument of claim 4, wherein said concave surface is arcuate.

6. The surgical instrument of claim 1, wherein said at least one cutter assembly is a plurality of cutter assemblies.

7. The surgical instrument of claim 6, wherein said plurality of cutter assemblies is a pair of blades.

8. The surgical instrument of claim 7, wherein a first of said pair of blades is disposed adjacent a first side of said stem and a second of said pair of blades is disposed adjacent a second side of said stem.

9. The surgical instrument of claim 8, wherein said first of said pair of blades is diametrically opposed to said second of said pair of blades about said stem.

10. The surgical instrument of claim 1, wherein:
    said at least one cutter assembly is configured to fit within an access tube when said at least one cutter assembly is in said fully retracted configuration; and
    said sleeve is translatable within said access tube so that said at least one cutter assembly is extendable beyond a distal end of said access tube.

11. The surgical instrument of claim 1 comprising a threaded insert disposed in and affixed to said sleeve, said threaded insert defining an internal thread, wherein:
    said stem includes an external thread that threadably engages said internal thread of said threaded insert;
    rotation of said stem portion in a first rotational direction about said actuation axis rotates said external thread relative to said internal thread, thereby causing said stem to translate through said proximal hub in said distal direction; and
    rotation of said stem portion in a second rotational direction that is opposite said first rotational direction about said actuation axis rotates said external thread relative to said internal thread, thereby causing said stem to translate through said proximal hub in said proximal direction.

12. The surgical instrument of claim 11, wherein said external thread defines a threaded region of said stem, said threaded region being contained in said sleeve during operation.

13. The surgical instrument of claim 1, wherein:
    said proximal hub defines an internal thread;
    said stem includes an external thread that threadably engages said internal thread of said proximal hub;

rotation of said stem portion in a first rotational direction about said actuation axis rotates said external thread relative to said internal thread, thereby causing said stem to translate through said proximal hub in said distal direction; and rotation of said stem portion in a second rotational direction that is opposite said first rotational direction about said actuation axis rotates said external thread relative to said internal thread, thereby causing said stem to translate through said proximal hub in a proximal direction.

14. The surgical instrument of claim 1, comprising:

a first threaded fitting coupled to a proximal end of said sleeve; and a second threaded fitting coupled to a proximal end of said stem, said first threaded fitting and said second threaded fitting being threadably engaged, wherein rotation about said actuation axis in a first rotational direction of said stem portion rotates said second threaded fitting relative to said first threaded fitting of said sleeve and causes said stem to translate through said proximal hub in said distal direction; and wherein rotation about said actuation axis of said stem portion in a second rotational direction that is opposite said first rotational direction rotates said second threaded fitting relative to said first threaded fitting of said sleeve and causes said stem to translate through said proximal hub in said proximal direction.

* * * * *